(12) United States Patent
Sondeen et al.

(10) Patent No.: US 8,409,130 B2
(45) Date of Patent: Apr. 2, 2013

(54) SYSTEM FOR PROVIDING SERVO-CONTROLLED RESUSCITATION

(75) Inventors: Jill L. Sondeen, New Braunfels, TX (US); Guy A. Drew, San Antonio, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 2478 days.

(21) Appl. No.: 10/935,640

(22) Filed: Sep. 8, 2004

(65) Prior Publication Data

US 2005/0101907 A1    May 12, 2005

Related U.S. Application Data

(60) Provisional application No. 60/500,889, filed on Sep. 8, 2003.

(51) Int. Cl.
*A61M 31/00* (2006.01)
(52) U.S. Cl. .................................................. 604/65
(58) Field of Classification Search .............. 604/65
See application file for complete search history.

(56) References Cited

U.S. PATENT DOCUMENTS

| | | | |
|---|---|---|---|
| 3,425,415 A | 2/1969 | Godron et al. | |
| 3,561,427 A | 2/1971 | Profy | |
| 3,749,285 A | 7/1973 | Latham, Jr. | |
| 3,999,542 A | 12/1976 | Shaw | |
| 4,137,915 A | 2/1979 | Kamen | |
| 4,286,590 A | 9/1981 | Murase | |
| 4,291,692 A | 9/1981 | Bowman et al. | |
| 4,392,849 A * | 7/1983 | Petre et al. | 604/66 |
| 4,457,751 A | 7/1984 | Rodler | |
| 4,467,844 A * | 8/1984 | Di Gianfilippo et al. | 141/1 |
| 4,494,950 A | 1/1985 | Fischell | |
| 4,688,577 A | 8/1987 | Bro | |
| 4,803,625 A | 2/1989 | Fu et al. | |
| 4,880,014 A | 11/1989 | Zarowitz et al. | |
| 4,908,350 A | 3/1990 | Kramer et al. | |
| 5,002,055 A | 3/1991 | Merki et al. | |
| 5,100,380 A | 3/1992 | Epstein et al. | |
| 5,116,312 A | 5/1992 | Blankenship et al. | |
| 5,142,484 A | 8/1992 | Kaufman et al. | |
| 5,269,301 A | 12/1993 | Cohen | |

(Continued)

FOREIGN PATENT DOCUMENTS

DE    199 55 368 A1    5/2001
FR    2 592 306 A1    7/1987

(Continued)

OTHER PUBLICATIONS

Abbod, M.F., et al., "Survey on the use of smart and adaptive engineering systems in medicine," Artificial Intelligence in Medicine, 2002, pp. 179-209, vol. 26.

(Continued)

*Primary Examiner* — Nicholas Lucchesi
*Assistant Examiner* — Jason Flick
(74) *Attorney, Agent, or Firm* — Elizabeth Arwine; Cahn & Samuels, LLP

(57) ABSTRACT

The present invention provides a system and method for controlling resuscitation in a patient. In at least one embodiment, the invention includes a fluid rate measurer, a controller electrically coupled to the fluid rate measurer, and a pump. The controller is adapted to receive signals from a physiological monitor and controls the pump.

26 Claims, 9 Drawing Sheets

U.S. PATENT DOCUMENTS

| | | | |
|---|---|---|---|
| 5,298,021 A | 3/1994 | Sherer | |
| 5,318,540 A | 6/1994 | Athayde et al. | |
| 5,331,549 A | 7/1994 | Crawford, Jr. | |
| 5,352,195 A | 10/1994 | McEwen | |
| 5,368,195 A | 11/1994 | Pleet et al. | |
| 5,584,806 A * | 12/1996 | Amano | 604/65 |
| 5,626,151 A | 5/1997 | Linden | |
| 5,733,259 A | 3/1998 | Valcke et al. | |
| 5,810,202 A | 9/1998 | Hoback et al. | |
| 5,827,219 A * | 10/1998 | Uber et al. | 604/30 |
| 5,882,207 A | 3/1999 | Lampotang et al. | |
| 6,010,454 A | 1/2000 | Arieff et al. | |
| 6,101,816 A | 8/2000 | Wang et al. | |
| RE36,871 E | 9/2000 | Epstein et al. | |
| 6,187,767 B1 | 2/2001 | Araneo et al. | |
| 6,280,408 B1 | 8/2001 | Sipin | |
| 6,682,481 B2 | 1/2004 | McKinley et al. | |
| 6,690,280 B2 | 2/2004 | Citrenbaum et al. | |
| 6,694,977 B1 | 2/2004 | Federowicz et al. | |
| 7,402,153 B2 | 7/2008 | Steil et al. | |
| 2002/0038392 A1* | 3/2002 | De La Huerga | 710/8 |
| 2002/0050142 A1 | 5/2002 | Wang et al. | |
| 2002/0058861 A1 | 5/2002 | Drew | |
| 2002/0143290 A1 | 10/2002 | Bui et al. | |
| 2003/0207464 A1 | 11/2003 | Lemmo et al. | |
| 2004/0258541 A1 | 12/2004 | Glatzmaier | |
| 2005/0143671 A1 | 6/2005 | Hastings et al. | |
| 2006/0134598 A1 | 6/2006 | Kenney | |

FOREIGN PATENT DOCUMENTS

| | | |
|---|---|---|
| FR | 2 682 602 A1 | 4/1993 |
| WO | WO 94/11054 | 5/1994 |

OTHER PUBLICATIONS

Aliabadi-Wahle S, Gilman, et al., "Effects of Vitamin C on Edema Formulation at the Site of Scald Injury," Proc. Am. Burn Assoc., 1996, p. 76, vol. 28.

Arieff, Allen I., "Fatal Postoperative Pulmonary Edema: Pathogenesis and Literature Review," CHEST Journal, May 1999, pp. 1371-1377, vol. 115.

Barrow, Robert E., et al., "Early Fluid Resuscitation Improves Outcomes in Severely Burned Children," Resuscitation, Jan. 11, 2000, pp. 91-96, vol. 45.

Baxter, Charles R, et al., "Physiological Response to Crystalloid Resuscitation of Severe Burns," Annals New York Academy of Sciences, 1968, pp. 874-894, vol. 150, No. 3.

Bert, J.L., et al., "Microvascular Exchange During Burn Injury: II. Formulation and Validation of a Mathematical Model," Circulatory Shock, 1989, pp. 199-219, vol. 28.

Bert, J.L., et al., "Microvascular Exchange During Burn Injury: IV. Fluid Resuscitation Model," Circulatory Shock, 1991, pp. 285-297, vol. 34.

Bert, L., et al. "Pressure-volume Relationship for Rat Dermis: Compression Studies," Acta Physiol Scand, 1997, pp. 89-94, vol. 160.

Bowman, R. J., et al., "A Microcomputer-Based Fluid Infusion System for the Resuscitation of Burn Patients," IEEE Transactions on Biomedical Engineering, Jun. 1981, pp. 475-479, vol. BME-28, No. 6.

Brandstrup, Birgitte, et al., "Effects of Intravenous Fluid Restriction on Postoperative Complications: Comparison of Two Perioperative Fluid Regimens A Randomized Assessor-Blinded Multicenter Trial," Annals of Surgery, Nov. 2003, pp. 641-648, vol. 238, No. 5.

Brunner, Josef X., "Principles and History of Closed-Loop Controlled Ventilation," Respiratory Care Clinics of North America, Sep. 2001, pp. 341-362, vol. 7, No. 3.

Cancio, Leopoldo C., et al., "Predicting Increased Fluid Requirements During the Resuscitation of Thermally Injured Patients," The Journal of TRAUMA, Feb. 2004, pp. 404-414, vol. 56, No. 2.

Chaisson, Neal F., "Near-Infrared Spectroscopy-Guided Closed-Loop Resuscitation of Hemorrhage," The Journal of TRAUMA Injury, May 2003, pp. S183-S192, vol. 54, No. 5.

Demling, Robert H., "Pulmonary Edema: Current Concepts of Pathophysiology, Clinical Significance, and Methods of Measurements," World Journal of Surgery, Apr. 1987, pp. 147-153, vol. 11.

Elgio, Geir Ivar, et al., "Burn Resuscitation with Two Doses of 4 mL/kg Hypertonic Saline Dextran Provides Sustained Fluid Sparing: A 48-Hour Prospective Study in Conscious Sheep," The Journal of TRAUMA, Apr. 5, 2000, pp. 251-265, vol. 49, No. 2.

Elgio, Geir Ivar, et al., "Hypertonic Saline Dextran Produces Early (8-12 hrs) Fluid Sparing in Burn Resuscitation: A 24-hr Prospective, Double-Blind Study in Sheep," Crit Care Med, 2000, pp. 163-171, vol. 28.

Elgio, Geir Ivar, et al., "Resuscitation with Hypertonic Saline Dextran Improves Cardiac Function in Vivo and Ex Vivo After Burn Injury in Sheep," SHOCK, 1998, pp. 375-383, vol. 9, No. 5.

Engrav, L. H., et al. "A Biopsy of the Use of the Baxter Formula to Resuscitate Burns or Do We Do It Like Charlie Did It?", Journal of Burn Care & Rehabilitation, Mar./Apr. 2000, pp. 91-95, vol. 21.

Hoskins, Stephen L., et al., "Closed-Loop Resuscitation of Burn Shock," Journal of Burn Care & Research, May/Jun. 2006, pp. 377-385, vol. 27, No. 3.

Ivy, Michael E., et al., "Intra-abdominal Hypertension and Abdominal Compartment Syndrome in Burn Patients," The Journal of Trauma, 2000, pp. 387-391, vol. 49.

Kramer, George C., et al., "Pathophysiology of Burn Shock and Burn Edema, "Herndon DN, ed. Total Burn Care. 2nd ed. New York: W.B. Saunders Company Ltd; 2002: 78-87.

Lee, Insup, "Case Study: Computer Assisted Resuscitation Algorithm (CARA) System", Department of Computer and Information Science University of Pennsylvania, Jun. 22, 2001, pp. 1-26.

Lowell, Jeffrey A., et al., "Postoperative Fluid Overload: Not a Benign Problem," Critical Care Medicine, 1990, pp. 728-733, vol. 18.

Murray, Michael J., et al., "Critical Care Medicine: Perioperative Management", 2002, pp. 803-804, Lippincott Williams & Wilkins, Second Edition.

Poli De Figueiredo, et al. "Hypertonic Acetate-ααHemoglobin for Small Volume Resuscitation of Hemorrhagic Shock," Art. Cells, Blood Subs., and Immob. Biotech., 1997 pp. 61-73, vol. 25.

Pruitt, Jr., Basil A., et al., "Fluid and Electrolyte Replacement in the Burned Patient," Surgical Clinics of North America, Dec. 1978, pp. 1291-1312, vol. 58, No. 6.

Pruitt, Basil Jr., "Protection of Excessive Resuscitation: "Pushing the Pendulum Back"," The Journal of Trauma, 2000, pp. 567-568, vol. 18.

Rafie, Abraham D., et al., "~Hypotensive Resuscitation of Multiple Hemorrhages Using Crystalloid and Colloids," SHOCK, Sep. 2004, pp. 262-269, vol. 22 No. 3.

Roa, Laura M., et al., "Analysis of burn injury by digital simulation," Burns, 1988, pp. 201-209, vol. 14, No. 3.

Shah, A., "Meta-Analysis of Fluid Requirements for Burn Injury 1980-2002," Journal of Burn Care Rehabilitation, 2003, p. S118, vol. 24.

Sondeen, Jill L., et al. "Hypotensive Resuscitation in a Model of Uncontrolled Hemorrhage in Swine," presentation at ATACCC 2002, 2002, slides 1-33.

Westenskow, Dwayne R., Ph.D. et al., "Microprocessors in intensive care medicine," Medical Instrumentation, Nov.-Dec. 1980, pp. 311-313, vol. 14, No. 6.

Wolf, Steven E., et al. "Mortality Determinants in Massive Pediatric Burns," Annals of Sugery, 1997 pp. 554-569, vol. 225, No. 5.

Ying, Hao, et al., "Fuzzy Control of Mean Arterial Pressure in Postsurgical Patients with Sodium Nitroprusside Infusion," Oct. 1992, pp. 1060-1070, vol. 39, No. 10.

"CARA Pump Control Software", Feb. 2, 1999, Doc Version 2.0, Rev. 5, pp. 1-13.

"CARA System Architecture Specification", Apr. 5, 1999, Doc. Version 1.0, Rev. 2, p. 1.

"CARA Pump Control Software" Jun. 18, 1999, Doc Version 4.0, Rev. 10, pp. 1-6.

"CARA Phase 1 Software Development Plan", Jul. 1, 1999, Version 1, pp. 1-12.

"CARA Increment 1", Jul. 7, 1999, Version 4.0, pp. 1-13.

"CARA Increment 2", Mar. 6, 2000, Version 1.7, pp. 1-11.

"CARA Pump Control Software", Jan. 25, 2001, Version 6.1, Rev. 4, pp. 1-10.
"CARA Increment 3 with Questions", Feb. 5, 2002, Version 1.1, pp. 1-11.
"CARA Increment 3", Apr. 8, 2004, Version 3.0, pp. 1-11.
"CARA Simulation: Overview of the Model", Oct. 7, 2004, Computer Website Article: http://bsd7.starkhome.cs.sunysb.edu/~cara/overview.html.

* cited by examiner

SYSTEM FOR PROVIDING SERVO-CONTROLLED RESUSCITATION

This application claims the benefit of U.S. provisional application Ser. No. 60/500,889, filed on Sep. 8, 2003, which is incorporated herein by reference.

I. FIELD OF THE INVENTION

The present invention relates generally to resuscitation, and more particularly to providing automated servo-controlled resuscitation.

II. BACKGROUND OF THE INVENTION

Studies have indicated that hemorrhage is one of the leading causes of death in conventional warfare. For example, some officials believe that hemorrhage accounts for approximately fifty percent of deaths occurring on the battlefield. It has been noted that effective first aid and proper fluid resuscitation strategies could prevent some of these casualties from occurring.

Therefore, resuscitation systems have been developed. For example, a typical resuscitation system may include a resuscitation pump which an operator (for example, a medic) utilizes to pump some type of revitalization fluid into the patient. Such systems often suffer from a variety of disadvantages.

For instance, as fluid is pumped into a patient based on the patient's condition, such pumps are often employed with a physiological device that can be utilized to monitor a patient's vital signs as the patient's condition changes. For example, it may be determined that a particular patient requires fluid resuscitation when his or her blood pressure falls below a particular low level. Until the blood pressure falls below the low level, the operator does not need to operate the resuscitation pump.

Similarly, when the patient's blood pressure reaches a particular high level, the resuscitation pump should not be operated. Although the user does not need to continuously operate the pump, it is imperative that the user activates the pump precisely when it should be activated (for example, when the patient's blood pressure falls below the particular low level) and deactivates the pump precisely when it should be deactivated (for example, when the patient's blood pressure reaches the particular high level). Otherwise, serious health risks may occur. For example, if the blood pressure rises too high, then a blood clot may be dislodged and bleeding may increase. On the other hand, if the blood flow is not high enough, an ischemia/reperfusion injury can occur, thereby possibly leading to brain damage, heart attacks and injury to other vital organs such as the liver, kidneys, and lungs.

Thus, the user must constantly and carefully monitor the physiological device to precisely determine when to activate and deactivate the pump. Such a task can be burdensome, as the user (for example, a medic on the battlefield) may be simultaneously responsible for several patients. The resuscitation process occurs over a long period of time (for example, a few hours) and the patient's status will fluctuate during this time, thereby resulting in fatigue on the part of the user and serious repercussions for the patient.

Yet another one of the drawbacks of traditional resuscitation systems relates to failure of the pump to maintain the pumping rate/level at which it was programmed to pump. For instance, a variety of events may occur during operation of the pump that may cause the pumping rate of the pump into the patient to be altered. For example, an increased venous pressure may slow the pump flow rate of the resuscitation fluid, or the tube that transports fluid from its container to the pump may experience stretching, thereby impacting the accuracy of the pumping rate/level. Failure of the resuscitation pump to maintain the pumping rate/level may also lead to the above-referenced health effects. Other problems may also occur such as if a particular dose of the fluid is required, inaccurate pumping rate could lead to an overdose or underdose being given.

Therefore, in light of the foregoing, what is needed is an automated and accurate system for controlling resuscitation.

III. SUMMARY OF THE INVENTION

The present invention provides an automated system for controlling resuscitation in a patient. In at least one embodiment, the invention includes a fluid rate measurer, a pump, a physiological monitor, and a controller coupled to the fluid rate measurer, the pump, and the physiological monitor. The controller is adapted to receive signals transmitted by the physiological monitor and is capable of executing a servo control computer program module for controlling the resuscitation pumping to maintain those values of the desired physiological variable range and an error correction computer program module for performing error correction of the resuscitation pump based on a relation of an amount of fluid expected to be pumped and an amount of fluid that is actually pumped by the pump.

A method for controlling resuscitation of a patient connected to a physiological monitor, the method comprising: receiving a physiological signal from a physiological monitor, the physiological signal is indicative of a physiological variable, sending a pumping signal to a pump based upon whether the physiological variable is below a target range for the physiological variable, receiving a flow signal from a measuring device, the flow signal is indicative of the rate of resuscitation fluid is being pumped into the patient; and performing error correction of the pumping signal based on the difference between an amount of fluid expected to be pumped and an amount of fluid that is actually pumped.

In at least one embodiment, the invention further includes a calibration module for performing an initial fluid flow rate calibration to determine a relationship between pumping volume and pumping voltage. Such a calibration assists in assuring that the pump is accurately pumping.

IV. BRIEF DESCRIPTION OF THE DRAWINGS

The use of cross-hatching or shading within these drawings should not be interpreted as a limitation on the potential materials used for construction. Like reference numerals in the figures represent and refer to the same element or function.

V. DETAILED DESCRIPTION OF THE DRAWINGS

A. Overview of System/Software

Figure 1A:
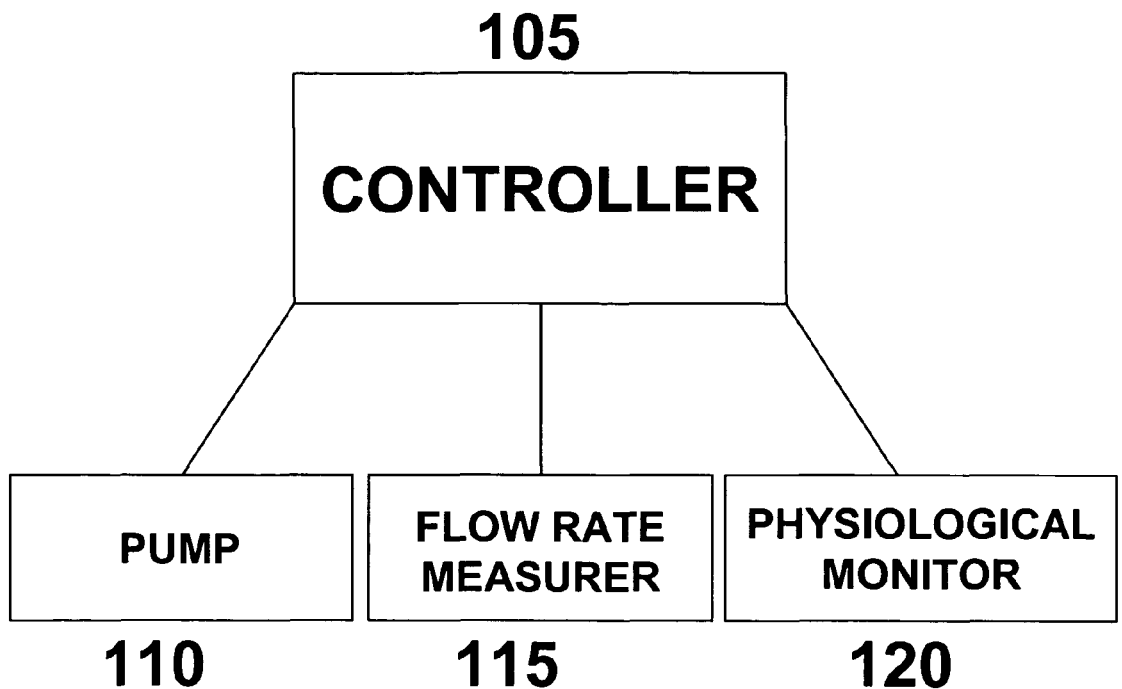
FIGS. 1A and 1B illustrate block diagrams of exemplary systems of the present invention.
Figure 1B:
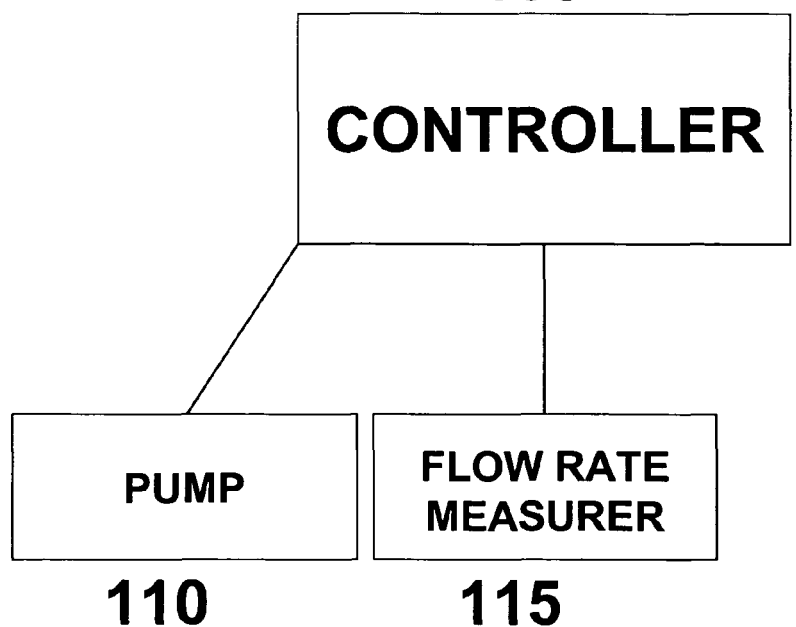

FIG. 1A illustrates a block diagram of an exemplary system 100 of the present invention. The system 100 may be utilized to automatically resuscitate a patient. In the embodiment of the invention illustrated in FIG. 1A, the system includes controller 105, pump 110, fluid flow rate measurer 115, and physiological monitor 120. FIG. 1 B illustrates another exemplary embodiment of the invention that includes the controller 105, the pump 110, and the fluid flow rate measurer 115.

The controller (or means for controlling) 105 controls operation of the system. In at least one embodiment, the controller 105 is a mainframe computer, minicomputer, personal computer, personal data assistant (PDA), or processing device as would be known to those of ordinary skill in the art after being presented with the disclosure herein. The controller 105 may, for example, execute software modules of the present invention. The software modules allow an operator to enter values according to which the system operates (for example, fluid flow rate for the pump 110) to automatically control resuscitation of a patient.

The software modules of the present invention preferably include a servo-controlled resuscitation module and a feedback/error correction module. The feedback/error correction module serves as an error correction means. The servo-controlled resuscitation module serves as a controlling means for automatically controlling the pumping means based on signals received from the physiological monitor and signal received from the error correction means. In at least one embodiment, however, the software modules of the present invention further include a connection/fluid rate calibration module (or means for calibrating fluid flow rate to determine a relationship between pumping volume and pumping voltage).

The pump (or means for pumping resuscitation fluid) 110 pumps fluid from a fluid container into a patient, thereby preferably resuscitating the patient. For example, in at least one embodiment, a tube extending from the container is connected to the pump 110. The pump 110 may be any resuscitation pump known to those of ordinary skill in the art. Examples of commercially available pumps include a MasterFlex roller pump (Cole Parmer Inc); a Power Infusion pump (Infusion Dynamics, Inc), a miniature IV resuscitation pump; or any standard hospital patient infusion pump in which two-way communication can be established with a computer. It should be noted in at least one embodiment that multiple pumps may be employed in the system of the present invention such that one pump pumps resuscitation fluid while a second or more pump(s) pumps medication or other material to the patient in addition to the resuscitation fluid.

The fluid flow rate measurer (or means for measuring a representation of fluid rate) 115 preferably determines the rate at which fluid is infused into the patient. Examples of the fluid flow rate measurer 115 include a flow meter that fits on the tubing, or a drip counter. The fluid flow rate measurer 115 may also be a balance 215 that is discussed in exemplary embodiments below.

The physiological monitor 120 monitors a physiological sign such as a vital sign (for example, arterial oxygen saturation, blood pressure, or heart rate). In at least one embodiment, the physiological monitor 120 includes a data acquisition system which can transmit physiological data such as systolic pressure to the controller. For example, the user may select to control the systolic pressure to 80±2 mmHg, in which a low systolic pressure limit of 78 mmHg below which the controller would turn on the resuscitation pump and a high systolic pressure limit of 82 mmHg above which the controller would turn the pump off. Any other monitored variable could be used to, for example, maintain arterial oxygen saturation at 90±2 percent or heart rate at 100±10 beats per minute. After being presented with the disclosure herein, those of ordinary skill in the relevant art will realize that the physiological monitor 120 may be any physiological monitor known to those of ordinary skill in the art and may monitor a variety of types of bodily functions of the patient.

Figure 2:
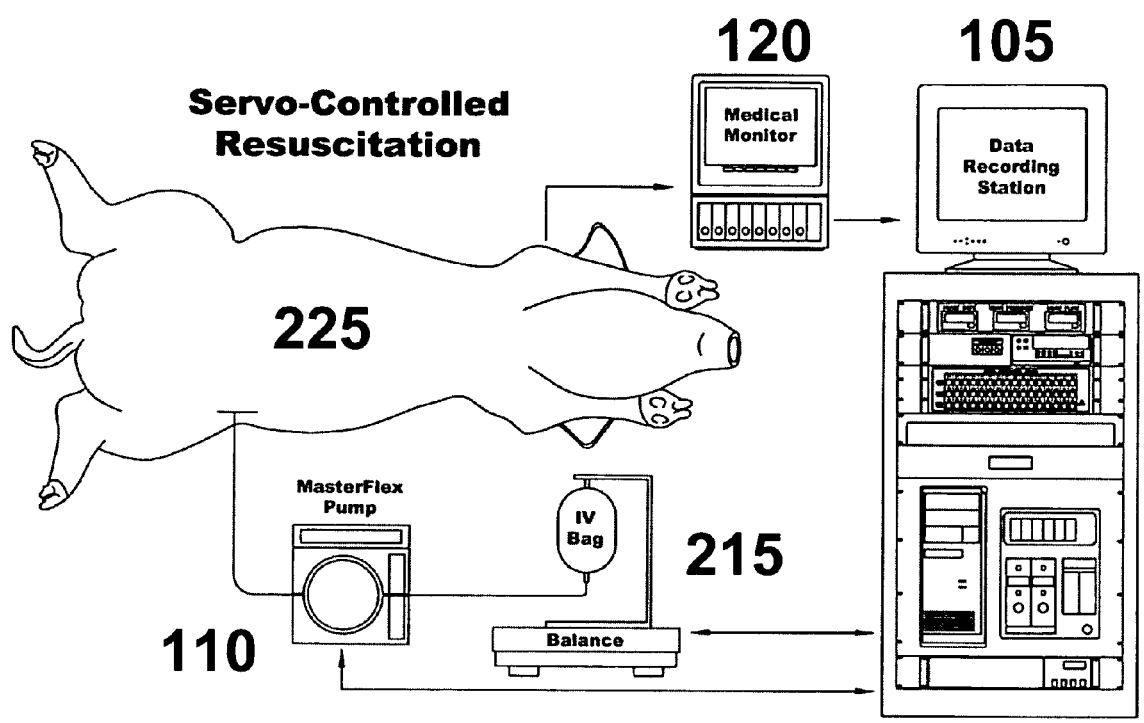
FIG. 2 illustrates a specific exemplary embodiment of the system of the present invention.

FIG. 2 illustrates a specific environment in which an exemplary system 200 of the present invention may be utilized to resuscitate a patient. The exemplary system 200 preferably includes the controller 105, the pump 110, a fluid weight balance 215, and the physiological monitor 120. The pump 110 is preferably coupled to a patient 225 through, for example, fluid lines and communicatively coupled to the controller 105 via, for example, an RS-232 connection. The fluid weight balance 215 is also communicatively coupled to the controller 105. Finally, the physiological monitor 120 is coupled to the patient 225 and communicatively coupled to the controller 105. Those skilled in the relevant art will realize that a variety of methods exist by which the components of the system 200 may be coupled together and to the patient 225. For example, the physiological monitor 120 may be coupled to the controller 105 by a communications cable or Wireless-Fidelity (Wi-Fi).

In the embodiment illustrated in FIG. 2, the fluid weight balance 215 preferably holds a container of fluid to be infused into the patient 225. For example, in at least one embodiment, the fluid weight balance 215 weighs a medical IV bag having hydration (or resuscitation) fluid. The fluid weight balance 215 may be any fluid weight balance known to those of ordinary skill in the art such as a Mettler balance with an analog or digital output that is provided to the controller 105.

Regardless of whether the present invention is implemented in hardware or software, an operator of the system of the present invention interacts with the system via at least one graphical user interface (GUI) executed on the controller 105. In at least one embodiment, the present invention includes a GUI for providing a main menu to an operator of the system. In such an embodiment, the GUI includes a list of menu options from which an operator may choose. The modules discussed above will be discussed below in exemplary implementations of the invention.

B. Servo-controlled Resuscitation Module

Figure 3:
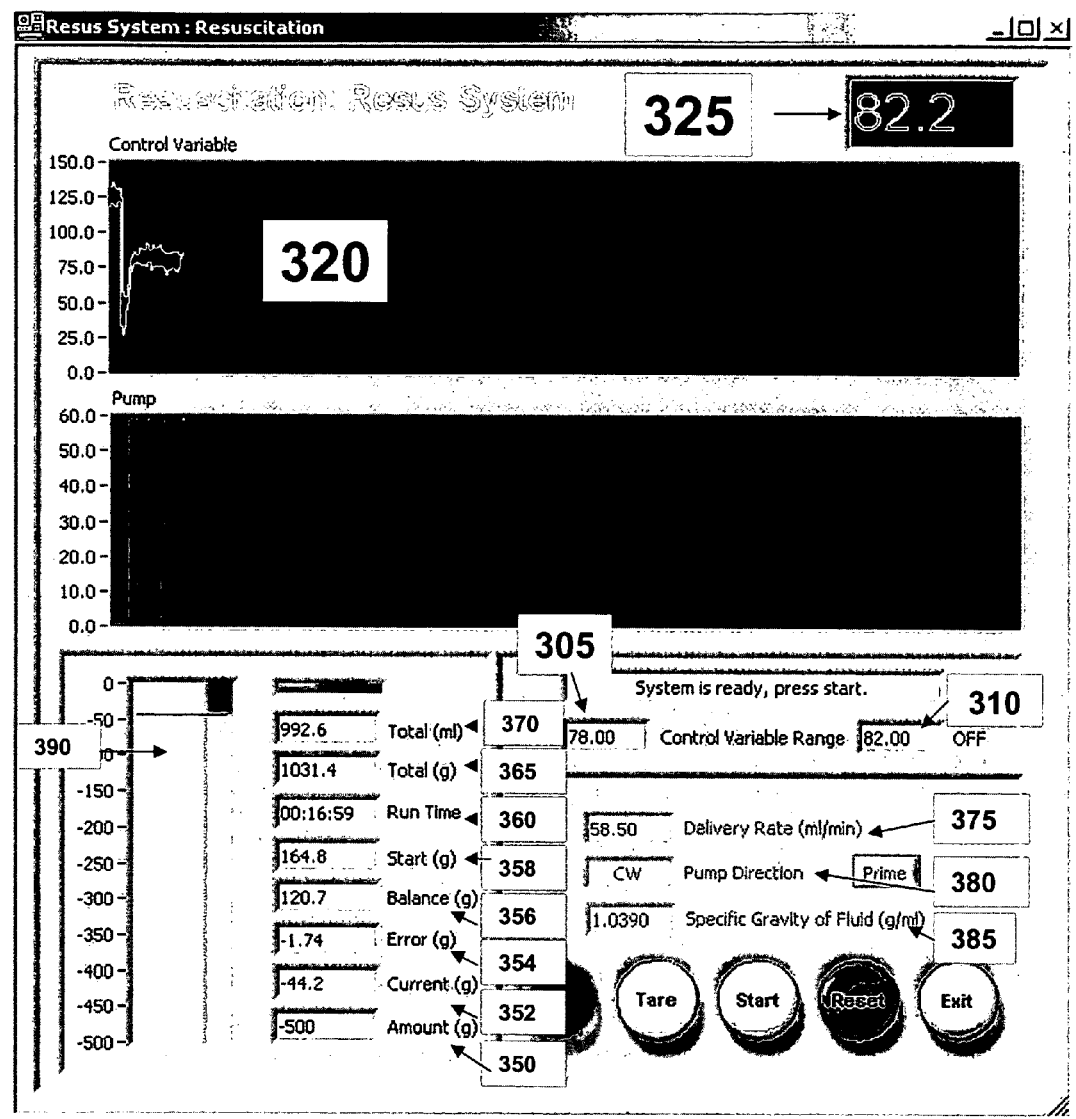
FIG. 3 illustrates a Graphical User Interface (GUI) depicting a servo-control resuscitation function according to at least one embodiment of the invention.

After the pump 110 has been calibrated, the operator preferably selects a resuscitation function option from the main menu GUI, thereby executing the servo-controlled resuscitation module of the present invention. For instance, FIG. 3 illustrates a GUI for the servo-controlled resuscitation module. Before the system of the present invention may operate, in at least one embodiment, the operator preferably selects a control variable, for example, a physiological variable such as systolic pressure as measured by the physiological monitor 120 attached to the patient, and enters a range for the control variable. The control variable range preferably determines when fluid will be infused into the patient. For example, as shown in FIG. 3, the operator has indicated a control variable range of 78.00 to 82.00. Thus, "on" data field 305 includes the value "78.00," and "off" data field 310 includes the value 82.00. Data fields 305 and 310 respectively are examples of means for allowing an operator to specify a low/high value for a physiological variable range.

Thus, the system will automatically activate when the physiological control variable is below a value of 78.00 and in one embodiment will continue to operate until the variable reaches a value of 82.00. Upon reaching the value of 82.00, however, the system will cease operation, as the endpoint (that is, the "off" value) has been obtained. In at least one embodiment, a trend line of the variable is electronically graphed, as shown in control variable graph section 320, and a current reading for the variable is displayed in window 325 (for example, every five seconds). In at least one embodiment, the control variable must read lower than the value entered into the "on" data field 305 for a number of cycles such as two data collection cycles (or for approximately ten seconds) to prevent the pump from cycling too frequently if there are transient changes. Similarly, the control variable must read higher than (or the same as) the value entered into the "off" data field 310 or be present in the operator selected range before the system deactivates. In at least one embodiment, the control variable must have exceeded (or be the same as) the value entered into the "off" data field 310 for two consecutive data collection cycles.

In at least one embodiment, in addition to entering a range for the control variable, the operator also selects or enters a constant infusion rate and a specific gravity of the fluid used (the purposes of which will be described herein below). In addition to these values, in at least one embodiment, the operator also preferably enters an "amount" value 350, a "delivery rate (ml/min)" value 375, a "pump direction" value 380, and a "specific gravity of fluid" value 385. The controller automatically keeps track of a "current" value 352, an "error" value 354, a "balance" value 356, a "start" value 358, a "run time" value 360, a "total (g)" value 365, and a "total (ml)" value 370. Each of these values will now be described in detail.

If the fluid measurer is a balance, the amount value 350 is preferably measured in grams. For other devices such as the flow meter or drip counter, the amount will be measured in the appropriate units (for example, ml/min or drips per minute, respectively). A positive value indicates that weight (fluid) will be added to the fluid weight balance (hemorrhaging simulation). A negative value indicates that fluid will be removed from the fluid weight balance (infusion). In at least one embodiment, the field into which this value is entered is disabled while fluid is actually being delivered. The current value 352 indicates the current amount of fluid delivered in grams for the current resuscitation session. In at least one embodiment, a cylinder bar status 390 is provided as a visual indication of how much fluid has been delivered for the given resuscitation session. The error value 354 indicates the delivery system error based on the difference between requested and actual delivery of fluid. A positive value indicates that the system has exceeded the appropriate delivery (too much). A negative value indicates that the system has not provided enough delivery.

The balance value 356 indicates the actual present weight of fluid in grams as indicated on the balance. The start value 358 indicates the weight on the fluid weight balance in grams at the start of a resuscitation session. The run time value (preferably measured in hours, minutes, and seconds) 360 indicates the total amount of time fluid has been delivered and is accumulative for all resuscitation sessions. The total (g) value 365 indicates an accumulative total weight in grams of fluid delivered for all resuscitation sessions. The total (ml) value 370 indicates a cumulative total volume in milliliters of fluid delivered for all runs. The specific gravity of fluid value 385 is measured in grams per milliliter and is used to calculate the actual milliliters per minute delivered based on grams over time. Once a resuscitation session has begun, the field into which the value is entered is preferably disabled. By having the computer cumulate multiple resuscitation sessions, the bags of fluid can be changed during the procedure, as is often necessary, and the total amount of fluid administered is monitored.

Alternatively, the data fields relating to weight and information from a balance may be replaced by data fields relating to a flow meter, a drip counter, or other fluid measurement devices as one of ordinary skill in the art will appreciate based on this disclosure. These fields provide information to the operator as to the status of the system and the resuscitation.

The delivery rate value 375 indicates the rate at which fluid is to be delivered in milliliters per minute. In at least one embodiment, after a resuscitation session has begun, the field into which the value is entered is disabled, as its value can only be changed at the start of a resuscitation session. The pump direction value 380 indicates the pump's rotation as clockwise (cw) or counter-clockwise (ccw).

In at least one embodiment, the GUI for the servo controlled resuscitation module preferably includes a panel of main control buttons. For instance, the buttons may include "stop," "tare" (used to clear the current (g) for a particular resuscitation session and load a new start (g) for a new resuscitation session in a balance implementation), and "start."

In at least one embodiment, the GUI for the servo-controlled resuscitation module preferably includes an electronic prime button for providing an operator with the ability to remotely prime the resuscitation pump and fluid lines (that is, tubing) without having to actually adjust the actual pump. In at least one embodiment, the GUI further includes a prime directional control, a prime rate control, a prime start control, and a prime exit control. The default prime rate is preferably equal to the resuscitation delivery rate for a resuscitation session.

A status indicator preferably provides information to an operator relating to the resuscitation session (for example, fluid level percentages as related to the amount (g) entered for delivery) according to at least one embodiment of the invention using the balance implementation. The indicator preferably changes color according to the status of the system. Exemplary colors are: (1) grey (system is ready; operator must press the start button to begin); (2) green (system is running and fluid delivery is normal); (3) yellow (less than forty percent of fluid specified to be infused is remaining in the fluid container on the fluid weight balance); and (4) red (less than twenty percent of fluid specified to be infused is remaining in the fluid container, or the stop limit has been reached and more fluid must be added to the system). In at least one embodiment, the color red may also indicate that the balance is not ready. A visual indicator may also be provided to allow an operator to determine how much fluid has been delivered for a given resuscitation session. The indicator may change colors depending on the fluid status. When a new reading is performed and values updated accordingly, an update indicator is preferably provided in at least one embodiment.

Figure 4:
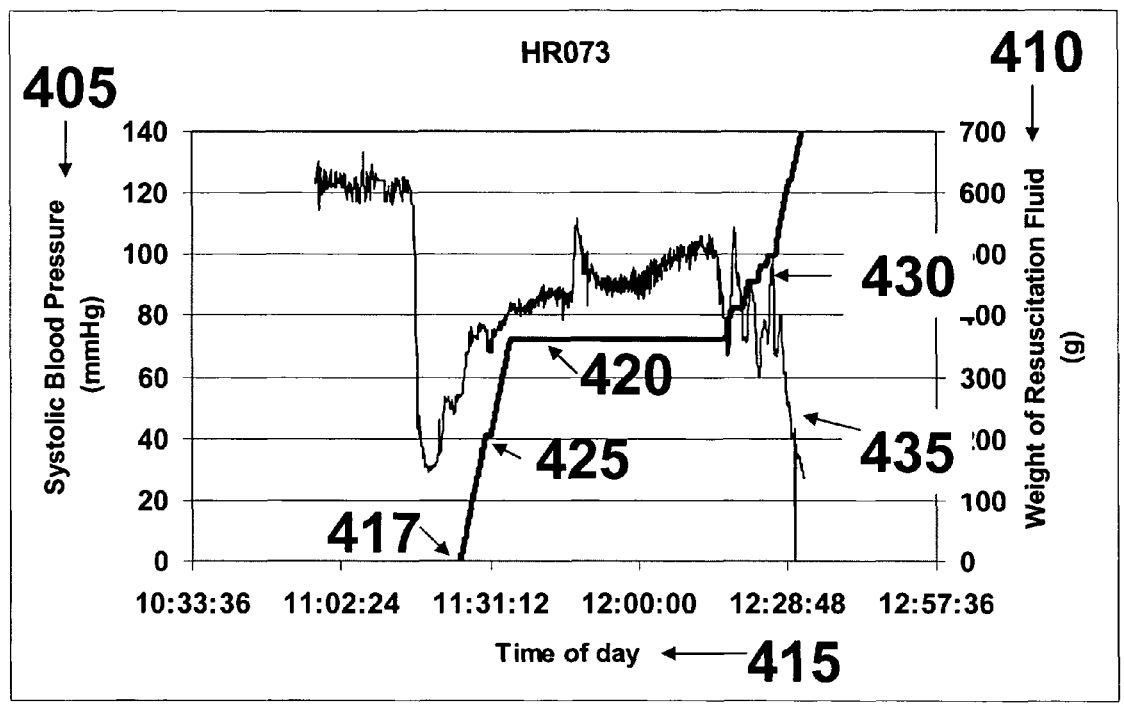
FIG. 4 illustrates an exemplary line graph visual display representing results of an actual test of the system of the present invention.

In at least one embodiment, the results of a resuscitation session may be provided in an electronic graph, as illustrated in FIG. 4. Systolic blood pressure variable 405 and weight of resuscitation variable 410 (in a balance implementation) are plotted on a line graph along with the time of day variable 415. As shown in FIG. 4, the graph preferably shows the cumulative weight of the resuscitation fluid during a session. Marker 417 indicates when the resuscitation session was started; marker 420 indicates when the resuscitation pump was turned off; marker 425 indicates when the resuscitation session was briefly paused to obtain a blood sample from a catheter; marker 430 indicates when the resuscitation pump was turned on and off around the target; and marker 435 indicates death of the patient.

The variables are preferably recorded in a text file and may be imported into another type of file (for example, Microsoft Excel) used to graph the data. In at least one embodiment, data is written to the text file every 5 seconds.

Additionally, any pattern of fluid administration (for example, an initially fast, then a slower rate as the target endpoint is approached) can be programmed into the computer for maximum flexibility. The system also saves all the data so that an accurate record of the fluid administered is automatically saved. Thus, in at least one embodiment, the system pumps according to data stored in a predetermined profile. For example, the profile data may include a target physiological range and infusion rates according to which the pump should operate.

Figure 5A:
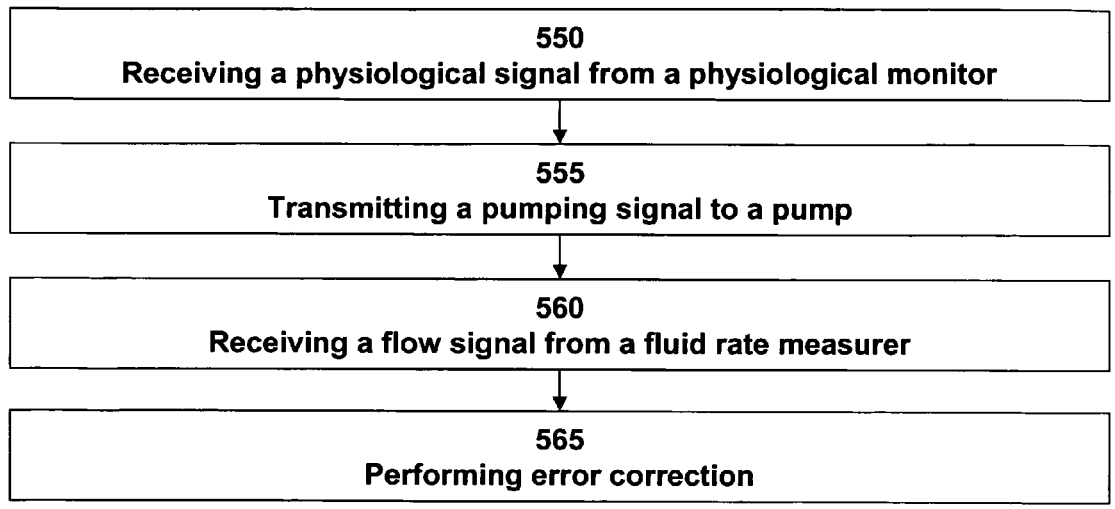
FIG. 5A is a flow diagram illustrating exemplary steps of an aspect of the present invention.

The invention also includes a method for performing resuscitation as illustrated in FIG. 5A. In step 550, the system receives a physiological signal from a physiological monitor, where the physiological signal is an indication of a physiological variable such as oxygen level, blood pressure, and pulse rate. Based on whether this physiological signal is below a target range for the physiological variable, a pumping signal (or control signal) is sent to the pump to activate it and pump resuscitation fluid into the patient as discussed above, step 555. The pumping signal is in the illustrated apparatus embodiments is a voltage, which level is determined based upon a look-up table for the particular pump and fluid line combination being used. In step 560, a flow signal is received from a measuring device such as the fluid rate measurer 115, where the flow signal is an indication of the actual rate that resuscitation fluid is being pumped into the patient. In step 565, a comparison is performed between the actual flow rate based on the flow signal and expected flow rate based on the pumping signal to determine an error correction value and thereafter adjust the pumping signal to bring into align the actual flow rate with the anticipated flow rate. An exemplary method for performing the error correction is illustrated in FIG. 5B and discussed below.

C. Feedback/Error Correction Module

Although the resuscitation pump is preferably calibrated before a resuscitation session, a variety of types of problems may occur during a resuscitation session to cause the pump not to operate at the programmed rate. For example, venous blood pressure or fluid line constriction may increase the back pressure which may affect the pump's output, the resuscitation pump may clot during pumping of a substance such as blood, and/or operation of the pump may be affected by the various viscosities (thickness) of different fluids. To compensate for these operational effects on the resuscitation pump, a feedback/error control module is provided in the system of the present invention. In summary, the feedback/error control module of the present invention compares the level of fluid measured by the fluid flow rate measurer 115 with the level of fluid expected if the pump was pumping at the set rate. In at least one embodiment, this comparison is performed and updated every five seconds.

Figure 5B:
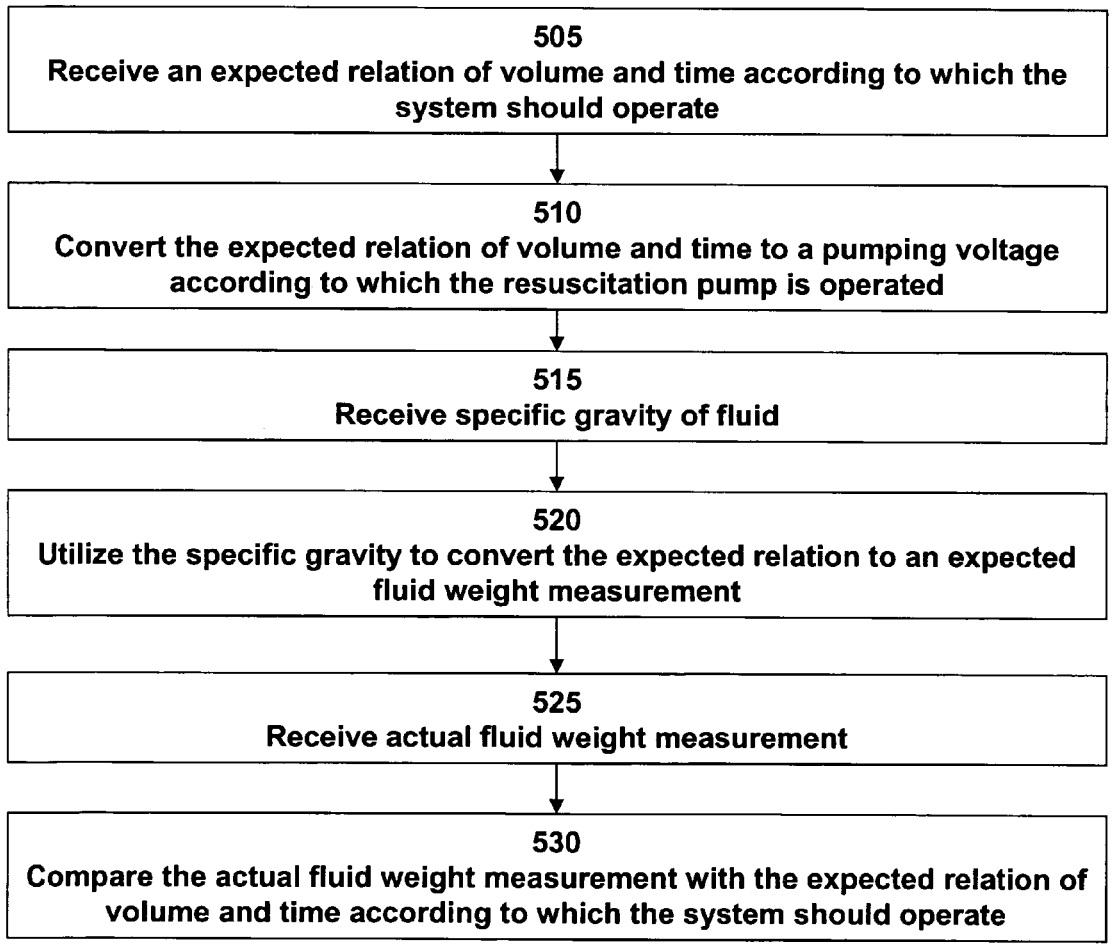
FIG. 5B is a flow diagram illustrating exemplary steps involved in obtaining feedback from the system for error correction according to the present invention.

FIG. 5B illustrates a flow diagram for steps involved in providing feedback for the system of the present invention in which a fluid weight balance 215 is utilized for the flow rate measurer 115. In step 505, an expected relation of volume and time (that is, the rate at which the user desires the pump to operate) according to which the system should operate is preferably entered into a system GUI, as described above in FIG. 3. For example, in at least one embodiment, the relation is entered in milliliters per minute, as shown in FIG. 3 (that is, delivery rate value 375). After being presented with the disclosure herein, those skilled in the relevant art(s) will realize, however, that the relation may be entered in any viable measurement.

In step 510, the expected relation of volume and time (e.g., milliliters/minute) is preferably converted to a pumping voltage according to which the resuscitation pump is operated. After being presented with the disclosure herein, those skilled in the relevant art will realize a variety of formulas and methods exist for converting the volume and time relation to a pumping voltage such as a look-up table or any other means for converting the expected relation of volume and time to a pumping voltage.

In step 515, a specific gravity of fluid value is received from the user. For instance, the specific gravity of fluid value 385 in FIG. 3, measured in grams per milliliter, is preferably received by the system from the user of the present invention. The field into which the specific gravity of fluid value 385 is an example of means for receiving a specific gravity of fluid value.

In step 520, the specific gravity of fluid value is utilized to convert the expected volume relation to an expected fluid weight measurement. After being presented with the disclosure herein, those skilled in the relevant art will realize that a variety of formulas and other means for utilizing the specific gravity of a fluid value exist for converting the expected relation to an expected fluid weight measurement.

In step 525, an actual fluid weight measurement is received into one of the fields (that is, a means for receiving the actual fluid weight measurement) of the GUI. That is, the fluid weight balance, for example, preferably transmits a signal including a weight value 356 for the fluid resting on the balance to the controller.

In step 530, the actual fluid weight measurement received in step 525 is compared with the expected fluid weight measurement calculated in step 520. After being presented with the disclosure herein, those of ordinary skill in the art will realize that a variety of methods (or means for comparing the actual fluid weight measurement with the expected fluid weight measurement) may be used to conduct the comparison. If the two values do not agree, an error term is preferably calculated and a rate is determined based on the difference between the two values. The software to perform this step is an example of means for determining a rate. The resuscitation pump is then instructed to either increase or decrease its speed according to the magnitude (that is, the value) and the direction of the error. When the error term equals zero (that is, there is no error), the pump is preferably instructed to pump at the set rate.

This error feedback method can work similarly for any device used to independently verify the accuracy of actual fluid dispensement (for example, the actual flow recorded by a flow meter will be used to generate an error term which will be used by the controller to adjust the flow rate of the system until the controlled flow rate equals the desired flow rate).

D. System Connection/Fluid Rate Calibration Module

Figure 6:
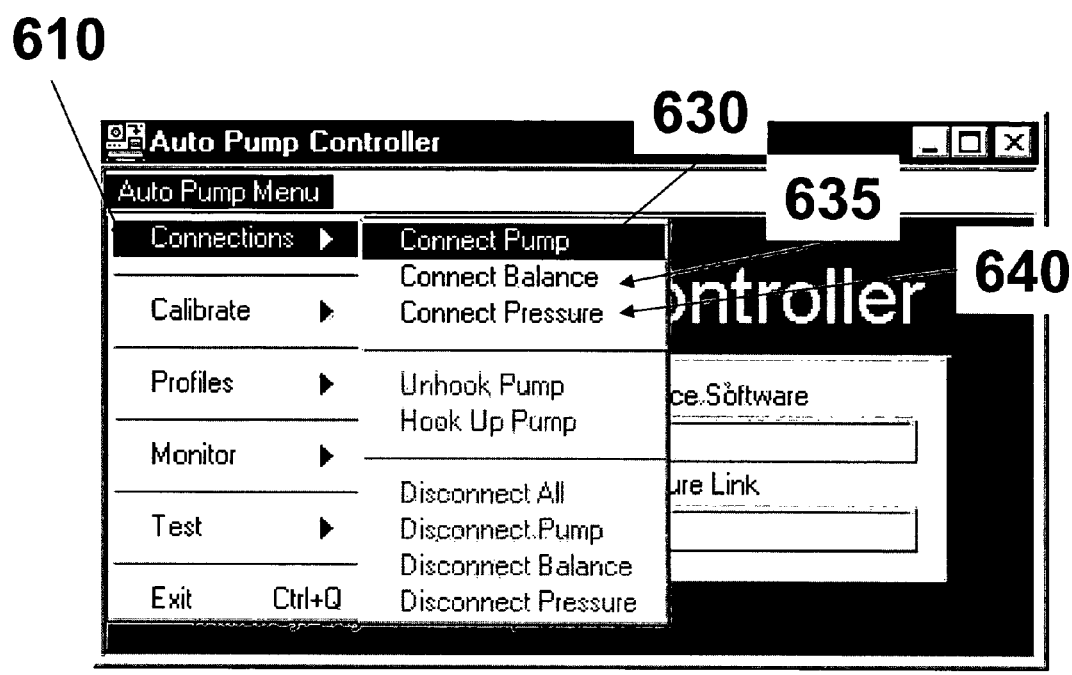
FIG. 6 illustrates a GUI depicting the connection function according to at least one embodiment of the present invention.

In at least one embodiment, prior to operation of the system, parameter values (for example, patient identification, date, body weight, or any other identifying information) are preferably entered into the appropriate areas of a demographics GUI of the system of the present invention. After the parameter values are entered, the software modules of the present invention preferably connect with the system 100, for example, the pump, the flow rate measurer, and the physiological monitor. For example, as shown in FIG. 6, a GUI menu is preferably provided with a "connections" menu/option 610. The connections menu 610 includes options for connecting components of the system. For example, in at least one embodiment, the connections menu 610 includes a connect pump option 630, a connect balance option 635, and a connect pressure option 640. As shown in FIG. 6, connecting a system component preferably includes three steps: (1) selecting the particular system component (for example, the pump or the balance); (2) selecting the particular communications port; and (3) pressing the connect electronic button. For instance, to connect the resuscitation pump to communications port, the operator selects the pump option 630 from the connections menu 610 and then selects the corresponding communications port to communicatively couple the pump device to the communications port via the software. As one of ordinary skill in the art will appreciate based on this disclosure, the initial set-up may be accomplished with automatic configuration such as plug and play.

Figure 7:
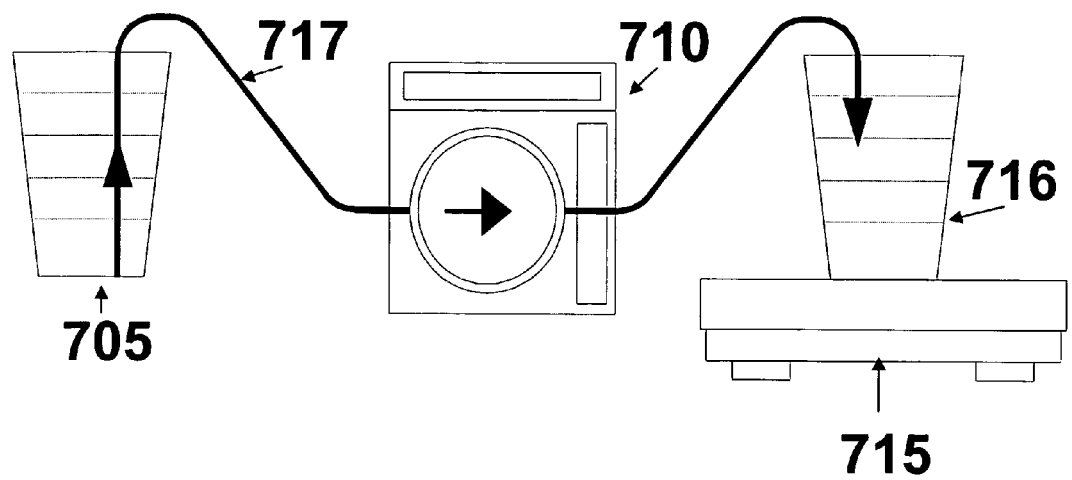
FIG. 7 illustrates an exemplary calibration setup system according to at least one embodiment of the present invention.

After the parameter values are entered into the system and the system components are connected, in at least one embodiment the system further includes a calibration module which serves as a means for calibrating the fluid flow rate (that is, automatic calibration). Calibration is performed to calibrate the rate at which fluid flows from the resuscitation pump. For example, FIG. 7 illustrates a basic calibration setup system 700 for calibrating the resuscitation pump. The calibration setup system 700 preferably includes a reservoir 705, a resuscitation pump 710, and a fluid weight balance 715. The reservoir 705 includes fluid and is connected to the intake of the selected tubing 717. The tubing 717 is routed through the pump 710 and into the receiving reservoir 716 on the fluid weight balance 715. In at least one embodiment, the operator preferably enters a variety of calibration parameters such as a tubing size value, a resuscitation pump direction value, a resuscitation pump cycle time value, a set point high value, and a set point low value. Appropriate calibration parameters would be programmed specific for each kind of pump used (for example, the MasterFlex pump used in this example, the Power Infuser rotary pump, or any standard patient intravenous fluid or syringe pump).

Figure 8:
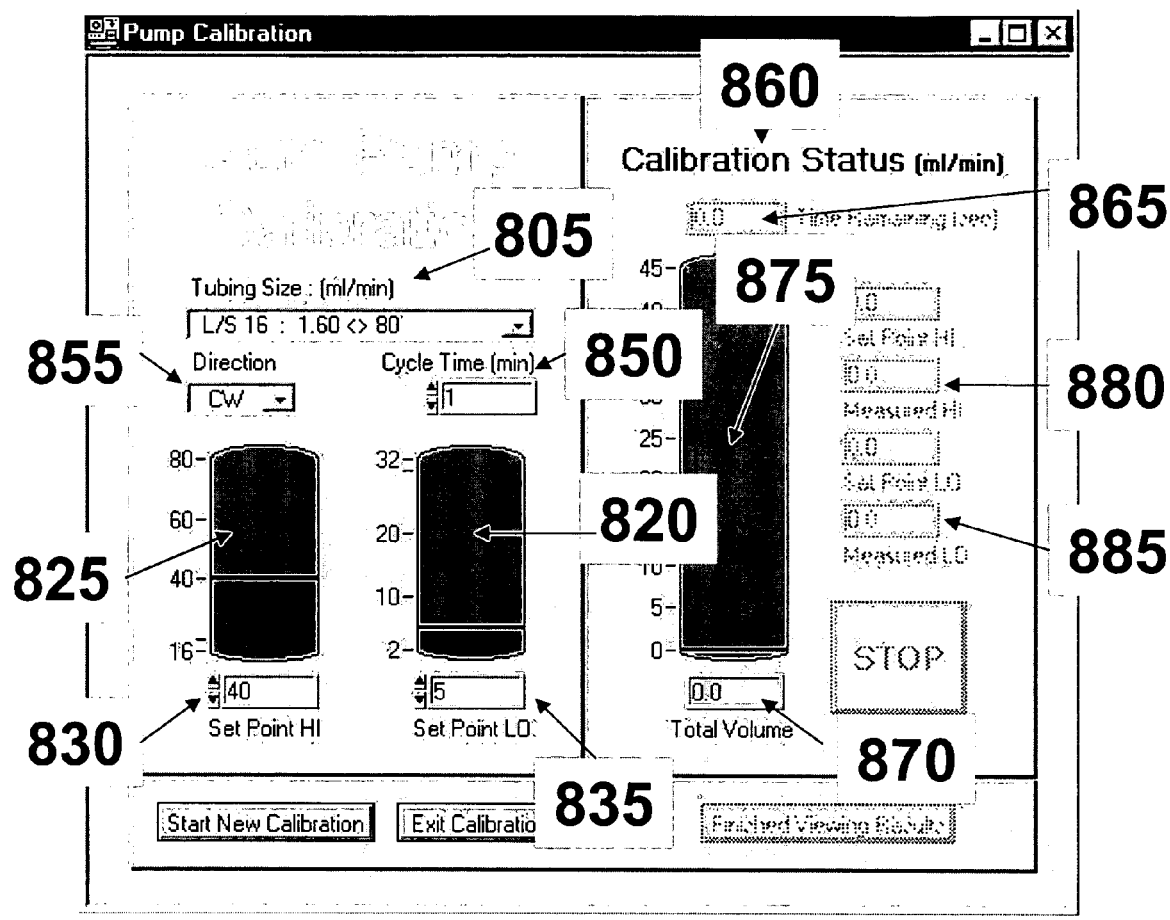
FIG. 8 illustrates a GUI depicting the automatic pump calibration function according to at least one embodiment of the invention.

FIG. 8 illustrates an exemplary GUI 800 for entering the calibration parameters. In "tubing size" field 805, a value for the size and/or type of tubing to be used to pump fluid from the fluid weight balance is entered. For instance, as shown in FIG. 8, the tubing size field 805 includes the value "L/S 16:1.60<>80". "L/S" refers to a specific type of biocompatible tubing, and the numbers following "L/S" refer to the tube manufacturer's (for example, Cole-Parmer) model number. The 1.60 and 80 are the minimum and maximum ranges in ml/min that the model of tubing is capable of pumping. Resuscitation pumps are dependent upon size and material of the tubing as to how accurately the pumps operate. The type of tubing preferably allows the fluid rate calibration function to determine the possible range of fluid delivery for the particular resuscitation pump. It should be noted that different pumps support different tubing sizes. Table 1 below indicates exemplary tubing sizes for a 100 RPM MasterFlex pump which provides greater accuracy at slow speeds and a 600 RPM MasterFlex pump that allows better accuracy at higher rates.

TABLE 2

Tubing Size vs. Pump RPMs

| 100 RPM MasterFlex Pump | 600 RPM MasterFlex Pump |
|---|---|
| L/S 13: 0.12 <> 6.0 | L/S 13: 0.60 <> 36.0 |
| L/S 14: 0.42 <> 21.0 | L/S 14: 2.10 <> 126.0 |
| L/S 16: 1.60 <> 80.0 | L/S 16: 8.00 <> 480.0 |
| L/S 25: 3.40 <> 170.0 | L/S 25: 17.0 <> 1020.0 |
| L/S 17: 5.60 <> 280.0 | L/S 17: 28.00 <> 1680.0 |
| L/S 18: 7.60 <> 380.0 | L/S 18: 38.00 <> 2280.0 |
| L/S 15: 3.60 <> 180.0 | L/S 15: 18.00 <> 1080.0 |
| L/S 24: 6.00 <> 300.0 | L/S 24: 30.00 <> 1800.0 |
| L/S 35: 8.60 <> 430.0 | L/S 35: 43.00 <> 2580.0 |
| L/S 36: 11.60 <> 580.0 | L/S 36: 58.00 <> 3480.0 |

Similar look-up tables can be included that are specific for each model and manufacturer of pump and tubing. In a production version of the device, the controller would be matched with a discrete set of pumps or a particular pump and tubing sizes as part of a standard set of equipment for medics.

In at least one embodiment, in addition to entering tubing size, the size of the pump head is preferably entered. The fluid rate calibration module of the present invention utilizes the tubing size value and the pump head size value to index an electronic table to obtain possible fluid rate ranges for the specified pump head size and tubing size. For example, the software may determine that for the entered tubing size and pump head size combination, the pump is capable of pumping from a low range 820 of 2-32 ml/min to a high range 825 of 16-80 ml/min.

For each of the offered low range 820 (that is, means for allowing an operator to specify a low value) and high range 825 (that is, means for allowing an operator to specify a high value), the operator may specify exact points in the particular range according to which the pump will be operated. For instance, for the high range 825, the operator may specify a setpoint high value 830 of 40 ml/min. Similarly, for the low range 820, the operator may specify a setpoint low value 835 of 5 ml/min. In at least one embodiment, the time at which the pump pumps at each of the setpoint high value 830 and the setpoint low value 835 is fixed. In the embodiment shown in FIG. 8, however, the time at which the pump will operate at the setpoint values may be adjusted by the operator of the system. For example, as shown in "cycle time" field 850, the pump will operate at each of the setpoint values for one minute. This allows the pump to be calibrated to be most accurate in the range of resuscitation flow rate that is expected to be used.

In at least one embodiment, the operator may also specify a direction for the pump head. For example, depending upon which direction fluid moves through the pump head, a clockwise (CW) or counter-clockwise (CCW) value may be entered into "direction" field 855.

As shown in FIG. 8, after calibration begins, the operator may check the status of the calibration via calibration status section 860. The calibration status section 860 displays a total calibration time (beginning at zero and counting up to a selected run time). In an alternative embodiment, the calibration status section 860 displays a total calibration time remaining in "time remaining" field 865. In at least one embodiment, a total calculated delivered volume of fluid is specified in "total volume" field 870 and displayed graphically in real-time in graphical display 875. At the end of the calibration cycle, an actual volume amount resting on the fluid weight balance 215 (shown in FIG. 2) is measured. "Measured high" indicator 880 and "Measured low" indicator 885 provide an actual amount of fluid delivered during each cycle. Thus, the operator may compare these values with the setpoints to determine whether to accept the calibration results or discard the calibration results based on the desired accuracy. That is, the setpoint high value 830 is preferably compared with the measured high indicator 880, and the setpoint low value 835 is preferably compared to the measured low indicator 885. If the desired accuracy was not obtained, the operator may choose to run another calibration cycle, as the software will use the current calibration results to perform adjustments for the next calibration run. Regardless of whether the user decides to execute another calibration run or functionally operate the system to resuscitate, the calibration results are saved in the system. It should be noted that the calibration may be aborted at any given time. In at least one embodiment, a previous calibration may be used, as all calibration results are saved in the system until they are cleared from the system.

Figure 9:
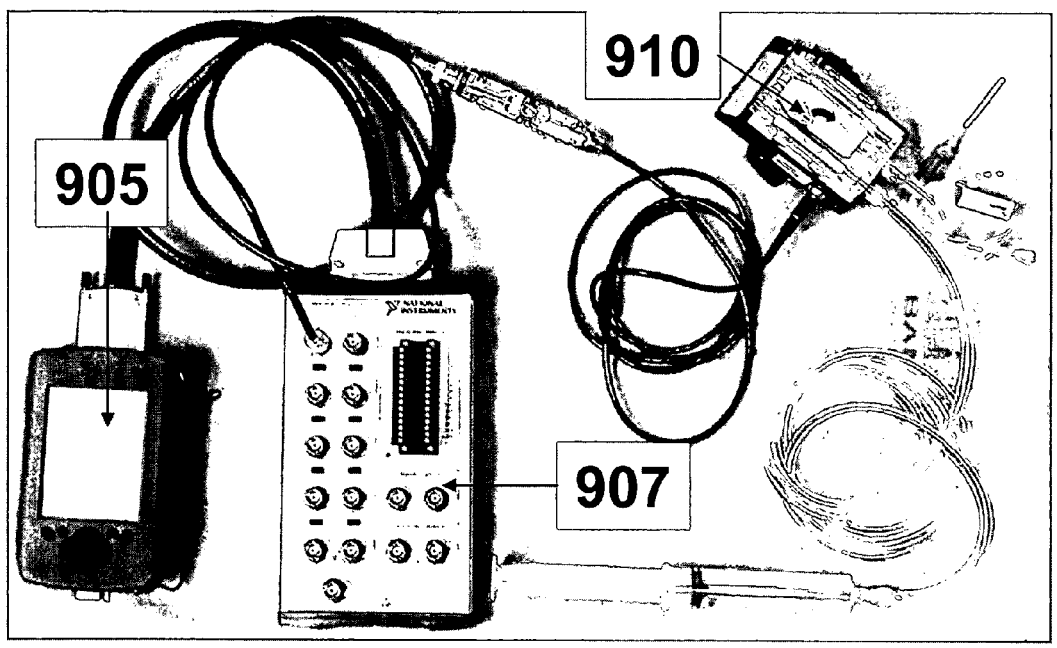
FIG. 9 illustrates an exemplary portable system according to at least one embodiment of the invention.

In at least one embodiment, the system of the present invention is a portable system, which may be utilized by a medic on a battlefield, for instance. For example, as shown in FIG. 9, system 900 preferably includes a pump 910, a portable controller 905, an interface box 907, and the flow rate measurer 115. The illustrated pump 910 is a small battery-powered Power Infuser portable pump.

In at least one embodiment, the portable controller 905 may be a Palm Pilot, a personal digital assistant, or any other viable mobile/portable controller. The system 900 illustrated in FIG. 9 is an exemplary test system. In an actual use environment (for example, on a battlefield), however, the interface box 907 would preferably not be an external device as displayed in FIG. 9. Rather, the interface box 907 would preferably be a miniature interface connector and reside in the portable controller 905 or alternatively be incorporated into the portable controller 905.

Those having ordinary skill in the art will recognize that the state of the art has progressed to the point where there is little distinction between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will appreciate that there are various vehicles by which processes and/or systems described herein can be effected (for example, hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and examples. Insofar as such block diagrams, flowcharts, and examples contain one or more functions and/or operations, it will be understood by those within the art that each function and/or operation within such block diagrams, flowcharts, or examples can be implemented, individually and/or collectively, by a wide range of hardware, software, firmware, or any combination thereof (or means for performing the respective function and/or operation). However, those skilled in the art will recognize that the embodiments disclosed herein, in whole or in part, can be equivalently implemented in standard Integrated Circuits, via Application Specific Integrated Circuits (ASICs), as one or more computer programs running on one or more computers (for example, as one or more server programs running on one or more computer systems), as one or more programs running on one or more processors (for example, as one or more thin client programs running on one or more processors), as firmware, or as virtually any combination thereof, and that designing the circuitry and/or writing the code for the software or firmware would be well within the skill of one of ordinary skill in the art in light of this disclosure. In addition, those skilled in the art will appreciate that the mechanisms of the present invention are capable of being distributed as a program product in a variety of forms, and that an illustrative embodiment of the present invention applies equally regardless of the particular type of signal bearing media used to actually carry out the distribution. Examples of a signal bearing media include, but are not limited to, the following: recordable type media such as floppy disks, hard disk drives, CD ROMs, digital tape, and transmission type media such as digital and analogue communication links using TDM or IP based communication links (for example, packet links).

The exemplary and alternative embodiments described above may be combined in a variety of ways with each other. Furthermore, the dimensions, shapes, sizes, and number of the various pieces illustrated in the figures may be adjusted from that shown.

Although the present invention has been described in terms of particular exemplary and alternative embodiments, it is not limited to those embodiments. Alternative embodiments, examples, and modifications which would still be encompassed by the invention may be made by those skilled in the art, particularly in light of the foregoing teachings.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

We claim:

1. An automated system for controlling resuscitation of a patient, comprising:
   a fluid rate measurer;
   at least one pump;
   a physiological monitor;
   an error correction means for performing error correction of said at least one pump based on a relation of an amount of fluid expected to be pumped and an amount of fluid that is actually pumped by said at least one pump as represented by signals received from said fluid rate measurer; and
   a controlling means for automatically controlling said at least one pump based on signals received from said physiological monitor and signal received from said error correction means.

2. The automated system of claim 1, further comprising a calibration module for performing an initial fluid flow rate calibration to determine a relationship between pumping volume and pumping voltage.

3. The automated system of claim 1, wherein said pump begins to pump only when the signal from said physiological monitor approaches or reaches the low value consecutively for two pump cycles and ceases to pump only when the signal from said physiological monitor approaches or reaches said high value consecutively for two pump cycles.

4. The automated system of claim 1, wherein said controlling means receives a signal representing the physiological variable in five second intervals during operation of the system.

5. The automated system of claim 1, wherein said error correction means includes determining a rate based on a difference between a level of fluid in a container weighed by said fluid rate measurer and an expected level of fluid to be in the container if the system were pumping as expected.

6. The automated system of claim 1, wherein said controlling means resides on a personal digital assistant (PDA).

7. The automated system of claim 1, wherein said pump includes a rotary infusion pump.

8. The automated system of claim 1, wherein said pump includes a resuscitation pump.

9. The automated system of claim 1, wherein said fluid rate measurer includes a flow meter.

10. A system for controlling resuscitation of a patient and connecting to a physiological monitor attached to the patient, said system comprising:
   a measuring means for measuring a representation of fluid rate;
   a pumping means for pumping resuscitation fluid into the patient;
   an error correction means for performing error correction of said pumping means based on a relation of an amount of fluid expected to be pumped and an amount of fluid that is actually pumped by said pumping means as represented by signals received from said measuring means; and
   a controlling means for automatically controlling said pumping means based on signals received from the physiological monitor and signal received from said error correction means.

11. The system of claim 10, further comprising a means for calibrating fluid flow rate to determine a relationship between pumping volume and pumping voltage.

12. The system of claim 10, wherein said controlling means includes means for allowing an operator to specify a low value for a physiological variable range.

13. The system of claim 12, wherein said controlling means further includes means for allowing an operator to specify a high value for the physiological variable range.

14. The system of claim 13, wherein said controlling means sends a signal to said pumping means to begin pumping only when the physiological variable reaches or is lower than the low value consecutively for two data collection cycles and a signal to cease pumping only when the physiological variable reaches or exceeds the high value consecutively for two data collection cycles.

15. The system of claim 10, wherein said controlling means polls the physiological monitor in five second intervals.

16. The system of claim 10, wherein said error correction means includes
   means for receiving an expected relation of volume and time according to which the system should operate;
   means for converting said expected relation of volume and time to a pumping voltage according to which said pumping means is operated;
   means for receiving a specific gravity of a fluid value;
   means for utilizing the specific gravity of a fluid value to convert the expected relation to an expected fluid weight measurement;
   means for receiving an actual fluid weight measurement; and
   means for comparing the actual fluid weight measurement with the expected fluid weight measurement.

17. The system of claim 10, wherein said error correction means includes means for determining a rate based on a difference between the level of fluid in a container weighed by said measuring means and the expected level of fluid to be in the container if the system were pumping as expected.

18. The system of claim 10, wherein said controlling means sends a signal to said pumping means to begin pumping only when the physiological variable reaches or is lower than the low value consecutively for two data collection cycles.

19. A system for controlling resuscitation of a patient comprising:
   a physiological monitor;
   a pumping means for pumping resuscitation fluid into the patient;
   a measuring means for measuring a representation of fluid rate pumped by said pumping means;
   an error correction means for performing error correction of said pumping means based on a relation of an amount of fluid expected to be pumped and an amount of fluid that is actually pumped by said pumping means as represented by signals received from said measuring means; and
   a controlling means for automatically controlling said pumping means based on signals received from said physiological monitor and signal received from said error correction means.

20. The system of claim 19, wherein said error correction means includes
   means for receiving an expected relation of volume and time according to which the system should operate;
   means for converting said expected relation of volume and time to a pumping voltage according to which said pumping means is operated;
   means for receiving a specific gravity of a fluid value;
   means for utilizing the specific gravity of a fluid value to convert the expected relation to an expected fluid weight measurement;
   means for receiving an actual fluid weight measurement; and
   means for comparing the actual fluid weight measurement with the expected fluid weight measurement.

21. The system of claim 20, further comprising a means for calibrating fluid flow rate to determine a relationship between pumping volume and pumping voltage.

22. The system of claim 20, wherein said controlling means includes means for allowing an operator to specify a low value for a physiological variable range.

23. The system of claim 22, wherein said controlling means further includes means for allowing an operator to specify a high value for the physiological variable range.

24. The system of claim 23, wherein said controlling means sends a signal to said pumping means to begin pumping only when the physiological variable reaches or is lower than the low value consecutively for two data collection cycles and a signal to cease pumping only when the physiological variable reaches or exceeds the high value consecutively for two data collection cycles.

25. The system of claim 20, wherein said controlling means polls the physiological monitor in five second intervals.

26. The system of claim 20, wherein said error correction means includes means for determining a rate based on a difference between the level of fluid in a container weighed by said measuring means and the expected level of fluid to be in the container if the system were pumping as expected.

* * * * *